United States Patent [19]
Plakas et al.

[11] 3,940,250
[45] Feb. 24, 1976

[54] TESTING USING LUMINESCENT REACTION

[75] Inventors: Chris J. Plakas, Washington, D.C.; George S. Glaros, Perama-Piraeus, Greece

[73] Assignee: Vitatect Corporation, Alexandria, Va.

[22] Filed: May 21, 1974

[21] Appl. No.: 471,854

Related U.S. Application Data

[63] Continuation of Ser. No. 222,256, Jan. 31, 1972, abandoned.

[52] U.S. Cl. ...... 23/230 B; 23/253 R; 195/103.5 R; 195/127; 356/36; 250/361
[51] Int. Cl.² C12K 1/10; G01N 33/16; G21H 5/00
[58] Field of Search ...................... 23/230 B, 253 R; 195/103.5 R, 127; 356/36; 250/304, 361, 364, 395, 428, 432, 483

[56] References Cited
UNITED STATES PATENTS

| | | |
|---|---|---|
| 2,741,544 | 4/1956 | Chaikin et al. ................. 23/232 R X |
| 3,155,451 | 11/1964 | Dunster et al. ................. 250/461 X |
| 3,288,995 | 11/1966 | Demorest ........................... 250/304 |
| 3,575,691 | 4/1971 | Pollard et al. ..................... 23/253 R |

*Primary Examiner*—Robert M. Reese

[57] ABSTRACT

A method and apparatus for testing a sample by means of luminescent reaction to detect reactive materials therein. A light-transparent filter is provided to filter the sample and to carry the residue to a reaction position. A light-transparent surface is provided to carry a reagent to the reaction position. Both surfaces are brought into mutual contact in a region between two photodetectors, which thereby detect the resulting luminescent reaction to provide an indication of the quantity of reactive material present in the sample.

13 Claims, 2 Drawing Figures

TESTING USING LUMINESCENT REACTION

This is a continuation of application Ser. No. 222,256 filed Jan. 31, 1972, and now abandoned.

BACKGROUND OF THE INVENTION

1. Field of the Invention

The present invention relates to a method and apparatus for detection of reactive material in a test sample and more specifically to an apparatus for detecting and measuring luminescence which occurs as a result of interaction between reactive materials and reagents.

2. Description of Prior Art

A great number of organic, inorganic and living materials may be detected by luminescent reaction techniques. Adenosinetriphosphate (ATP) has been found in all forms of living organisms and the average amount of ATP contained in each species of cells is well defined, thus making ATP an indicator of living materials. By measuring ATP, the number and size of microbial cells can be easily computed. Enzyme contained in the firefly tail is used as an reagent for detecting ATP and consequently for detecting microorganisms. When the firefly enzyme extracted from the firefly tail, known as luciferase luciferin, is mixed with ATP from microorganisms, a reaction takes place with luminescent emission of light. The light emitted is proportional to the quantity of ATP provided sufficient enzyme is present for the reaction of the total ATP. Luminescence also occurs during interaction of microbial cells with reagents such as luminol-peroxide.

All known current methods for detection of bioluminescence and chemiluminescence used in pollution control and clinical applications are based on the use of a reaction chamber where sample and reagents are introduced for reaction and luminescent emission, a photomultiplier is used to detect luminescence, and a data recording unit records luminescence. These methods have limited resolution and sensitivity due to losses of light in transmission from the reaction chamber to the photo-detector, self-absorption of luminescence in the reaction chamber, and photodetector noise. The present invention is an improvement upon copending U.S. Pat. application Ser. No. 29,475, filed Apr. 17, 1970, and entitled "Luminescence Detection by Surface Reaction now U.S. Pat. No. 3,690,832," which disclosed a new way of detecting the reaction of very small volumes of sample and reagent by use of a surface reaction and of coincidence circuitry. The present invention is an improvement upon this method and provides a sample filtration unit and a reagent dilution unit. Furthermore, the function of the present invention as a scintillation detector has been improved by the use of liquid scintillator for greater instrument capability at a lower cost.

SUMMARY OF THE INVENTION

It is therefore the object of the present invention to provide a rapid method of optically detecting the reactive material in a test sample by filtering the sample, concentrating the residue on a light transparent filter for direct contact with reagent, and thus eliminating time-consuming cultivation procedures.

Another object of the invention is to provide an apparatus for diluting dry enzyme within the instrument to thus preserve its potency until the time of use.

Another object of the invention is to provide an improved surface reaction instrument comprising a fluid supply unit, filtration unit, extraction unit, reagent dilution and supply unit, detection unit, and recording unit, all operating together to accurately measure the reaction of reactive materials carried on a filter surface when direct contact is made with reagents carried on a transparent surface.

DESCRIPTION OF THE PREFERRED EMBODIMENTS

Figure 1:
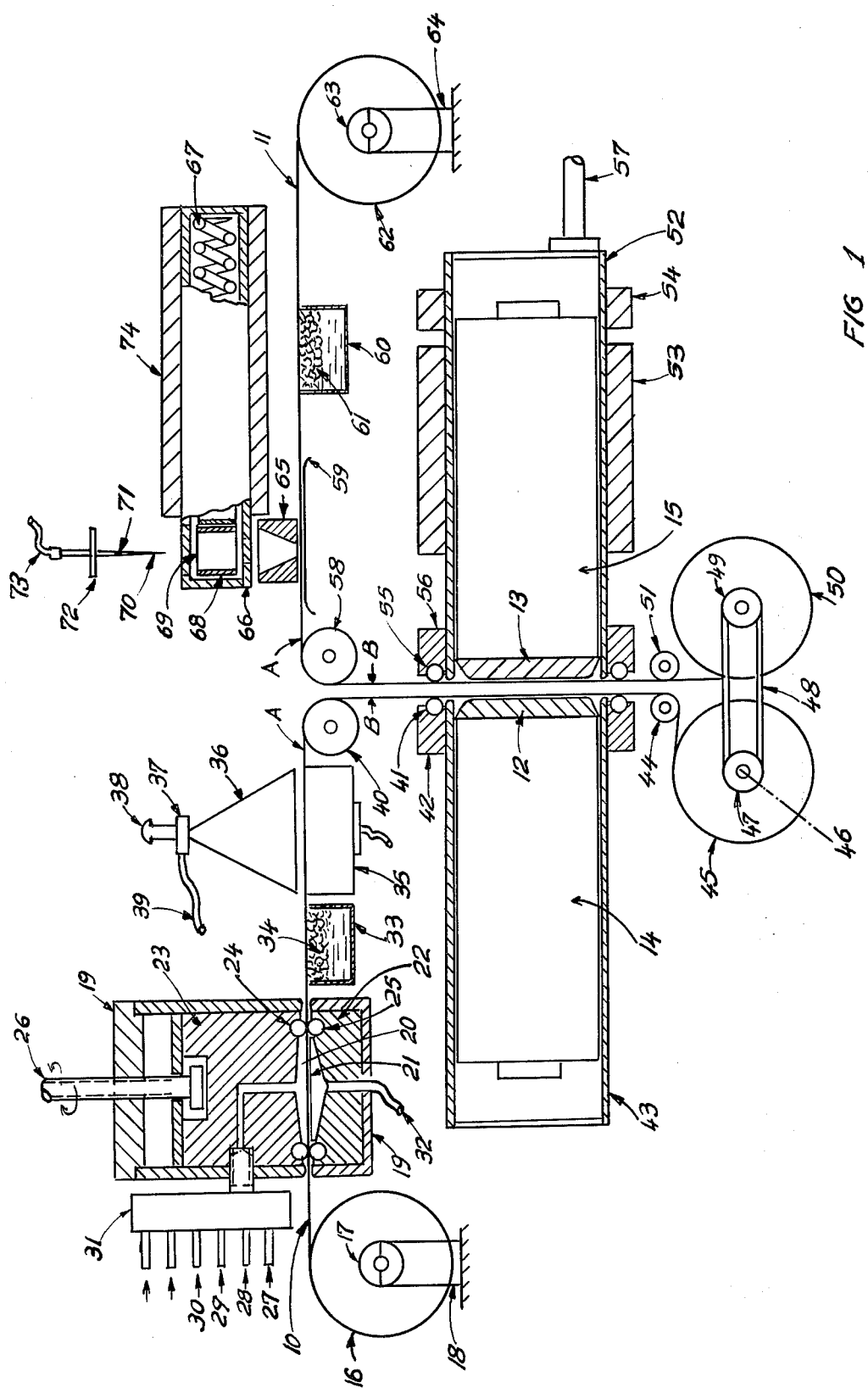
FIG. 1 is a schematic diagram of a surface reaction apparatus illustrating the principles of operation according to a preferred embodiment of the invention.

Referring now to FIG. 1 of the drawings, for detection of bioluminescent reaction according to the preferred embodiment of the invention, a light-transparent filter 10 begins its motion from a supply reel 16, passes through a sample filtration unit 19 where sample-containing reactive materials are forced through the filter, then advances between extractors 35 and 36 and carries the residue in the form of an aquatic layer between photodetectors 14 and 15 for reaction. A light transparent film or surface 11 begins its linear motion from a supply reel 62, passes under a reagent feeder 65, 66 and carries the reagent in the form of an aquatic layer between the photodetectors 14 and 15. Face A of filter 10 bearing reactive material and face A of surface or film 11 bearing the reagent are drawn together between the photodetectors 14 and 15. As the reagent medium and reactive material contact each other, a reaction occurs, and the resulting luminescence is transmitted to the photodetectors through the transparent films via coupling liquid and light pipes.

Now, with more specific reference to the operation of the system for bioluminescent detection, the reel 16 supplies a light transparent flexible porous filter 10 in the form of a film. Filter film 10 may be made of cellulose or other plastic materials of high optical transparency. Also, materials that become transparent when their pores are filled with samples or liquids of the same refractive index may be used effectively. The thickness of the material should be between 50 microns and 500 microns for greatest effectiveness, although other thicknesses may be used. Mean flow pore size should be between 0.007 and 5 microns depending on the nature of the specific experiment. Filter film 10 passes through the filtration unit 19 comprising blocks 22 and 23, their respective seals 24 and 25, an activator 26 for positioning block 23 selectively to free or seal the filter film 10, a cavity 20 being formed when block 23 is in the sealed position, and a grill 21 to support the filter film 10 and thus to enable it to resist differential pressure as the sample is forced through the pores of the filter.

The sample, whether liquid or gas, is introduced through one of the inlets 27 or 28, comprising one-way valves fitted in the block 31, and waste is drained through a hose 32. Block 31 contains additional inlets, such as 29 and 30 for introduction of different fluids necessary for residue preparation of various sample materials. Blocks of different sizes may be substituted to permit adjustment of filtration area while preserving sterile conditions.

After the filtration process is complete, the filter film 10 with the residue on face A passes over a coupling liquid feeder 33 where optical coupling liquid is deposited on face B of filter film 10. The coupling liquid may be any transparent liquid having a refractive index comparable to that of the filter film and the light pipes. A coupling liquid stored in container 33 saturates a sponge 34, which contacts face B of the filter film 10 and applies the coupling liquid to facilitate light transmission from the reaction surfaces to the light pipes.

Filter film 10 stops when the residue area is between extractors 35 and 36, to permit extraction of the test sample, which may contain a plurality of biological cells, such as those of certain microorganisms. When ultrasonic extraction is selected as the more effective means of disruption of cells of microorganisms of certain species, transducer 35 radiates ultrasonic energy which is transmitted through the coupling liquid to the residue on face A of filter film 10. Under ultrasonic oscillation, disruption of microbial cells occurs, releasing the adenosinetriphosphate compound, which reacts with the firefly enzyme when they come in contact between the photo-detectors. When chemicl extraction is selected, an activator 38 operates a spray valve 37 connected to an aerosol container (not shown) by a hose 39. Valve 37 sprays a fine mist of liquid solution such as butanol, dimethyl sulfoxide, acetone, or other extracting liquid through a guide funnel 36.

Filter film 10 travels over a guiding roller 40 and transports the residue between the lightpipes 12 and 13 for reaction process. The lightpipes are coupled to the photocathodes of the photomultipliers with mineral oil, silicon oil, Canada balsam or other similar liquid to insure good optical contact. After the luminescent reaction is recorded, the filter film 10 continues its motion around a guiding roller 44 and is collected on a storage reel 45 which is operated through an extension shaft 46.

Figure 6:
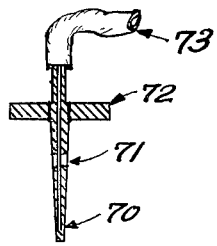
FIGS. 6, 7, and 8 illustrate the enzyme dilution and supply unit as used in the system of FIG. 1.
Figure 7:
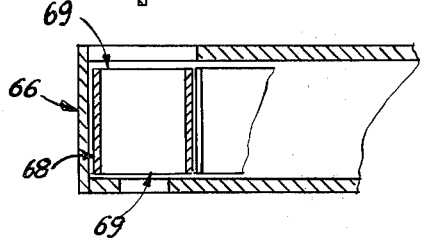
Figure 8:
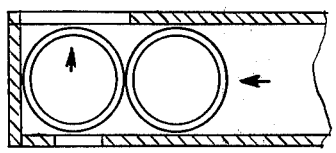

The description following concerns the path of film 11 carrying the reagents, such as firefly enzyme (luciferaseluciferin). A reel 62 supplies the light transparent film 11 of high optical transparency. Film 11 passes over a container 60 filled with a sponge material 61 saturated with optical coupling liquid, which is applied to face B of the film 11. The reagent is deposited on face A of film 11 by a reagent feeder 65,66. When an enzyme is used as the reagent, it is stored in a frozen lyophilized state in cylindrical cuvettes or tubes such as cuvette 68, sealed on both sides with sterilized protective paper 69. An injection needle 70, located over the cuvette, has lateral injection holes 71 and a disc 72 of soft material mounted rigidly on the needle 70, which is connected with a metering pump (not shown) through tube 73 to supply dilution liquid. As the needle is lowered into the cuvette, breaking both the protection papers, the disc 72 seals the upper opening to prevent leakage. Dilution liquid is injected into the cuvette through holes 71 and dilutes the dry enzyme. The enzyme solution drops into feeder guide 65 and wets face A of film 11 with a uniform aquatic layer as film 11 moves between guide 65 and a support 59. When the needle 71 is raised, cuvette 68 is disposed of through a side port (see FIG. 6) and a new cuvette is pushed into position by a spring 67. Another way of supplying reagent is to prepare film 11 with a dry reagent adhering to face A at evenly spaced intervals and to dilute it at the reagent feeder position. Some dry reagents may be used even without dilution. For example dry firefly enzyme gives a satisfactory reaction when direct contact is made with a wet residue. However firefly enzyme should be kept at low temperatures whether applied dry to the film or stored in cuvette for dilution. A thermoelectric element 74 maintains cuvette 68 at a desired temperature.

Film 11 continues its motion over a guide roller 58 and brings the reagent between the photodetectors 14 and 15 for the reaction process. After the reaction is completed, the film 11 passes over a guide roller 51 and is collected on a storage reel 50.

Figure 3:
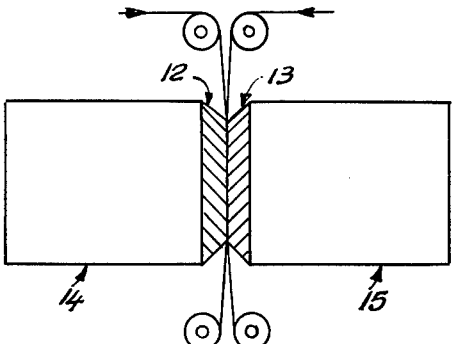
FIG. 3 is a cross-sectional view of light pipes suitable for use in the embodiment of FIG. 1 for conducting a total reaction experiment.
Figure 5:
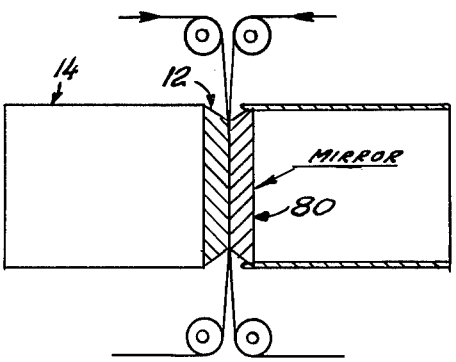
FIG. 5 is a cross-sectional view of a similar setup using a reflecting mirror as in FIG. 4 and suitable for use in place of the system of FIG. 3 for total reaction experiments.

For recording total luminescence of the filtration area the faces A of the transparent films are not permitted to contact while in motion. When the films reach the reaction position between the photodetectors, they stop. Assembly 52, operated by an actuator 57 and a non-illustrated mechanism, moves toward an assembly 43, and faces A of film 10 and 11 contact each other and a reaction takes place. Assembly 52 slides free in the frame 53, and the fixed position of the ring 54 controls the clearence between the two films to that the reactive and reagent materials will make contact but will not be displaced. After the reaction is completed and the results are recorded on a chart recorder or display tube (not shown), assembly 52 is reset, thereby freeing the films 10 and 11 to be collected on their respective storage reels. Ring 42 and seal 41 of assembly 43 and ring 56 and seal 55 of assembly 52 touch each other and protect the photodetectors from ambient light during the reaction process and during instrument repairs. Films 10 and 11 are respectively maintained in constant tension by pressure blocks 17 and 63 and by tension cords 18 and 64. FIGS. 3 and 5 show the preferred geometrical shape of light pipes used in combination respectively with two photomultiplers or with one photomultiplier for measuring total reaction. Light pipes permit uniform response by photomultipliers, but satisfactory experiments may be performed without them.

Figure 2:
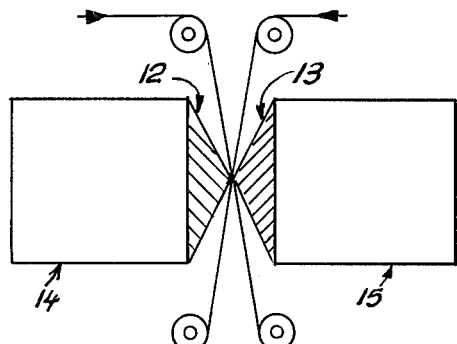
FIG. 2 is a cross-sectional view of light pipes suitable for use in the embodiment of FIG. 1 for conducting an individual-cell reaction experiment.
Figure 4:
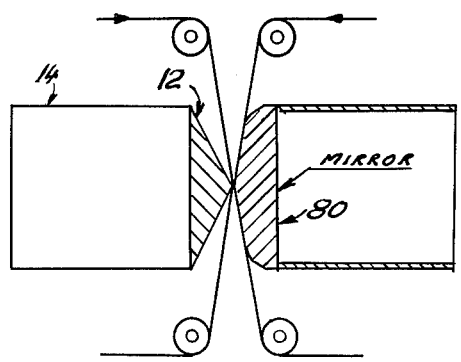
FIG. 4 is a cross-sectional view of an alternative setup of the system of FIG. 2 using one photomultiplier and a reflecting mirror for individual cell reaction experiments.

For recording individual cell reaction, narrow-edged light pipes are used as shown in FIGS. 2 and 4, and the clearance between them is preadjusted so that the faces A of the respective films 10 and 11 will contact, forming a series of reaction lines across the width of the moving films. For counting individual cells, the cell density per ml of the sample should be very low in order to achieve a good statistical sample value on the counter. The number of microbial cells can be computed even with a total reaction experiment if the kind or size of bacterial cells is known.

Operational procedures for chemiluminescent experiments are similar to those described above with the exception that chemical compounds such as luminol peroxide, alkaline luminol, or luminol perborate are used as reagents instead of the enzymes, and therefore, the residues do not require extraction. Usually, chemical reagents are applied through the tube 73 and the needle 70 directly into the guide 65. However, chemical reagents may be diluted by the same procedure as used with dry enzymes.

The surface reaction apparatus is also capable of measuring the level of fluorescence when biological samples carrying labeled carbon or other isotopic products are interacted with liquid scintillation materials. The set-up for this experiment is similar to that for bio-chemi-luminescence with the exception that the light transparent film 11 carries a liquid scintillator such as aromatic or water miscible solvent base, supplied by needle 70. The apparatus achieves high sensitivity in fluorescent measurement due to coincidence circuitry and due to the fact that radioactive materials are totally wetted with scintillation liquid and therefore no radiation is absorbed by the filter film, as happens when filter paper is used.

The surface reaction system can be used with no modification for detecting metal ions in water and air by precipitating the substance to be determined with tagged reagents. For example, metal ions precipitated with reagents $S_{35}$, and $P_{32}$ and $I_{131}$, form a stable compound. The precipitant may be filtered through the filtration unit to remove excess amounts of reagent and to retain the compound on the filter. The compound is washed with a neutral liquid to remove free particles of tracer and then the measured activity of the compound will be proportional to the amount of the substance precipitated.

For special, high-accuracy experimental work, the films may be replaced by light transparent plates, one of which is a filter. In another alternative, the instrument may be operated using only one photodetector. By using a mirror 80 at the back of one light pipe instead of the usual lightpipe-photomultiplier assembly, luminescence is reflected back toward the active photomultiplier. The mechanism for adjusting the clearance between the light-transparent surfaces is necessary and can be the same as that described for use with two photomultipliers. The single photomultiplier-mirror arrangement may be used for all of the experiments. However, two photo-multiplier tubes give better resolution especially for scintillation fluorescence.

The transparent film needed for this system to provide the transparent surface may be made of cellulose, such as cellophane, and can be obtained commercially from Dupont and other manufacturers. The transparent filter material can be made of the same materials, and can be obtained commercially from Gelmar Instrument Co. of Ann Arbor, Michigan.

We claim:

1. A method of optically detecting the presence of biological cells as reactive materials in a sample containing a plurality of biological cells comprising the steps of:
  A. filtrating said sample on a light-transmitting filter to produce a filtrate containing biological cells from the sample,
  B. rupturing the cells in the residue while on said filter,
  C. depositing a reagent on a light-transmitting surface,
  D. bringing said surface and said filter into contact for luminescent reaction, and
  E. detecting said luminescence as an indication of said biological cells as reactive materials present in said sample.

2. A surface reaction system for detecting reactive materials in a test sample containing a plurality of individual biological cells by means of luminescent reaction, comprising:
  A. means for filtering said sample through a filter to produce a residue containing biological cells from the sample,
  B. extraction means for rupturing the cells in the residue while on said filter,
  C. means for bringing reagent material into contact with the ruptured cells on the filter to cause reaction and consequent bioluminescence, and
  D. detector means for measuring and indicating the intensity of the bioluminescence, thereby indicating the quantity of biological cells in the sample.

3. A surface reaction system for detecting biological cells as reactive materials in a test sample containing a plurality of biological cells by means of luminescent reaction, comprising:
  A. means for filtrating said sample through a light-transmitting filter to produce a residue containing biological cells from the sample,
  B. extraction means for rupturing the cells in the residue while on said filter,
  C. means for depositing reagent material on a light-transmitting surface,
  D. means for bringing said light-transmitting filter with the ruptured cells of said residue thereon into contact with said light transmitting surface with said reagent material thereon, thereby allowing reaction and consequent luminescence, and
  E. detector means for recording the intensity of said luminescence, thereby indicating the quantity of biological cells as said reactive materials present in the sample.

4. The system of claim 3 wherein said means for filtrating sample through a light-transmitting filter further comprises:
  A. a filtration unit to guide the sample through said filter,
  B. supply inlets to introduce said sample and any other fluids necessary for preparation of residues, and
  C. means for mechanically operating and positioning said filter.

5. The system of claim 3 wherein said light-transmitting filter is a light-transmitting filter film for filtrating sample and carrying the residue in adjustable areas between the photodetectors for reaction.

6. The system of claim 3 wherein said means for depositing reagent materials on a light-transmitting surface further comprises means for supplying and diluting dry enzyme and for applying a resulting enzyme solution in a uniform layer of adjustable area on said light-transmitting surface.

7. The system of claim 3 wherein said means for depositing reagent materials on a light-transmitting surface further comprises means for adhering dry reagent to one face of said light-transmitting surface.

8. The system of claim 3 wherein said means for depositing reagent materials on light-transmitting surface further includes means for applying liquid scintillator in a uniform layer on said surface.

9. The system of claim 3 wherein said means of bringing said light-transmitting filter and said light-transmitting surface into contact comprises:
  A. means for guiding said transmitting surfaces between a pair of photodetectors, B. means of controlling motion of said filter and said surface, and C. means for continuously supplying and storing said surface and said filter.

10. The system of claim 3 wherein said surface and said filter both comprise light-transmitting plates.

11. The system of claim 3 wherein said detector means further comprises:

A. two photomultiplier tubes with coincidence circuitry,

B. light pipes,

C. optical coupling liquid, and

D. means for adjusting the space between the light pipes, said coupling liquid allowing low-refraction coupling of said luminescence to said light pipes, the light pipes coupling said luminescence to the photomultipliers.

12. The system of claim 3 wherein said detector means comprises a plurality of pairs of interchangeable light pipes with one face equal in area to that of the sensitive face of the photomultiplier tube and the opposite face equal in area to that of the desired reaction area for coupling light from a reaction area of any desired size to the photomultiplier.

13. The system of claim 3 wherein said detector means comprises one photodetector in combination with light pipes, one of said light pipes carrying reflecting mirror means and means to adjust the clearance between the light-transmitting surfaces.

* * * * *

Disclaimer 3,940,250.—*Chris J. Plakas*, Washington, D.C., and *George S. Glaros*, Perama-Piraeus, Greece. TESTING USING LUMINESCENT REACTION. Patent dated Feb. 24, 1975. Disclaimer filed Feb. 13, 1976, by the assignee, *Vitatect Corporation*.

Hereby enters this disclaimer to claim 2 of said patent.

[*Official Gazette May 25, 1976.*]